(12) United States Patent
Kuesters et al.

(10) Patent No.: US 7,569,698 B2
(45) Date of Patent: Aug. 4, 2009

(54) PROCESS FOR THE ISOLATION AND PURIFICATION OF EPOTHILONES

(75) Inventors: Ernst Kuesters, Eschbach (DE); Heinz Unternaehrer, Kaiseraugst (CH)

(73) Assignee: Novartis AG, Basel (CH)

( * ) Notice: Subject to any disclaimer, the term of this patent is extended or adjusted under 35 U.S.C. 154(b) by 345 days.

(21) Appl. No.: 11/205,892

(22) Filed: Aug. 17, 2005

(65) Prior Publication Data

US 2005/0288514 A1    Dec. 29, 2005

Related U.S. Application Data

(62) Division of application No. 10/433,808, filed as application No. PCT/EP01/14771 on Dec. 5, 2001, now Pat. No. 6,946,561.

(30) Foreign Application Priority Data

Dec. 7, 2000    (GB)    ................... 0029895.0

(51) Int. Cl.
    *C07D 277/22*    (2006.01)
(52) U.S. Cl. .................... 548/203; 548/204
(58) Field of Classification Search ........... 548/203, 548/204
    See application file for complete search history.

(56) References Cited

U.S. PATENT DOCUMENTS 6,946,561 B2 *    9/2005    Kusters et al. ............. 548/203

FOREIGN PATENT DOCUMENTS

| WO | WO 93/10121 | 5/1993 |
|---|---|---|
| WO | WO 98/22461 | 5/1998 |
| WO | WO 99/42602 | 8/1999 |

OTHER PUBLICATIONS

Nicoud et al., "Simulated Moving Bed (S.M.B.): Applications for Enantiomer Separations on Chiral Stationary Phases," Proceedings of the 1$^{st}$ European Meeting on Simulatd Moving Bed Chromatography, pp. 65-88 (1993).
Küsters et al., "Enantioseparation of a Chiral Epoxide by Simulated Moving Bed Chromatography Using Chiralcel-OD," Chromatographia, vol. 40, pp. 387-393 (1995).
Gerth et al., "Epothilons A and B: Antifungal and Cytotoxic Compounds from *Sorangium cellulosum* (Myxobacteria) Production, Physico-chemical and Biological Properties," Journal of Antibiotics, vol. 49, pp. 560-563 (1996).
Nicolaou et al., "Probing the Ring Size of Epothilones: Total Synthesis of [14]-, [15]-, [17]-, and [18] Epothilones A," Angew. Chem. Int. Ed., vol. 37, No. 1/2, pp. 81-84 (1998).
Nicolaou et al., "Chemical Biology of Epothilones," Angew. Chem. Int. Ed., vol. 37, pp. 2014-2045 (1998).
Reichhardt C., Organic Chemistry, 2$^{nd}$ Ed., p. 60, XP 002192137 (1988).
Snyder, L.R. et al., "Classification of the Solvent Properties of Common Liquids," Journal of Chromatographic Science, vol. 16, pp. 223-234 (1978).
Robinson et al., "Liquid-Solid Chromatography on Amberlite XAD-2 and Other Styrene-Divinylbenzene Adsorbents," Journal of Chromatography, vol. 189, pp. 145-167 (1980).
Gerth et al, The Journal of Antibiotica, vol. 49(6), pp. 560-563 (1996).

* cited by examiner

*Primary Examiner*—Rei-tsang Shiao
(74) *Attorney, Agent, or Firm*—George R. Dohmann

(57) ABSTRACT

The invention relates to a desorption process for epothilones, especially epothilone A and/or epothilone B, from resins and new production, work-up or purification processes or manufacturing methods for epothilones comprising said desorption process, as well as the use of certain solvents for the desorption of epothilones from resins.

5 Claims, No Drawings

PROCESS FOR THE ISOLATION AND PURIFICATION OF EPOTHILONES

This application is a divisional of U.S. patent application Ser. No. 10/433,808, filed Jun. 6, 2003, which is a 371 of International Application No. PCT/EP01/14771, filed Dec. 5, 2001.

The invention relates to a new desorption process for epothilones, especially epothilone A and/or epothilone B, from resins and new production, work-up or purification processes or manufacturing methods for epothilones comprising said desorption process, as well as the use of certain solvents for the desorption of epothilones from resins.

BACKGROUND OF THE INVENTION

Epothilones A and B represent a new class of microtubuli-stabilising cytotoxic active ingredients (see Gerth, K. et al., J. Antibiot. 49, 560-3 (1966)) of the formulae:

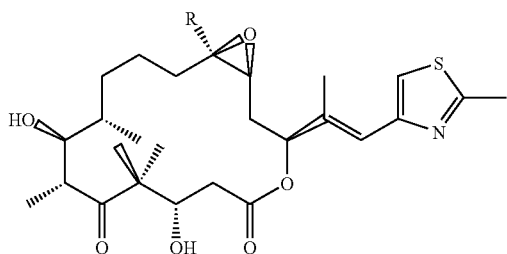

wherein R signifies hydrogen (epothilone A) or methyl (epothilone B).

Since the description of these epothilones (see WO 93/10121), several methods have been disclosed for the synthesis and manufacture both of the epothilones and mainly of numerous epothilone derivatives (collectively called "epothilones" hereinafter), for example those disclosed in WO 99/03848, WO 00/49020, WO 00/49021, WO 00/47584, WO 00/00485, WO 00/23452, WO 99/03848, WO 00/49019, WO 99/07692, WO 98/22461, WO 99/65913, WO 98/38192, WO 00/50423, WO 00/22139, WO 99/58534, WO 97/19086, WO 98/25929, WO 99/67252, WO 99/67253, WO 00/31247, WO 99/42602, WO 99/28324, WO 00/50423, WO 00/39276, WO 99/27890, WO 99/54319, WO 99/54318, WO 99/02514, WO 99/59985, WO 00/37473, WO 98/08849, U.S. Pat. No. 6,043,372, U.S. Pat. No. 5,969,145, WO 99/40047, WO 99/01124, and WO 99/43653. In addition to epothilone A and epothilone B, especially the epothilones D and E, described in WO 97/19086 and WO 98/22461, and the epothilones E and F, described in WO 98/22461, as well as the epothilones described in WO 99/02514 show interesting properties.

As an example for the therapeutic use, International Application WO 99/43320 describes a number of ways of administration of epothilones as agents against proliferative diseases, especially tumor diseases, that, due to their similar mechanism, act in a way comparable to that of Taxol®, a well-known and marketed anticancer agent. WO 99/39694 discloses some specific formulations of the epothilones, especially A and B.

The epothilones, especially epothilone A and most preferably epothilone B, offer a number of advantages in comparison to established treatments, especially also in cases where tumors have become refractory to the treatment with Taxol. Therefore, methods for their synthesis in larger amounts are urgently required in order to meet anticipated demands.

The most efficient production processes so far at least comprise some biosynthetic steps and isolation of epothilones from culture media or the like.

Originally, the extraction of natural substances by means of myxobacteria, especially the epothilones from the cell strain *Sorangium Cellulosum Soce*90 (deposited under no. 6773 at the German Collection of Microorganisms, see WO 93/10121) was described in literature. In order to obtain a satisfactory concentration of the natural substances, especially the epothilones, previously an adsorbate resin based on polystyrene was always added to the culture medium for absorption to the medium, for example Amberlite XAD-1180 (Rohm & Haas, Frankfurt, Germany).

However, the disadvantage of this process is that, on a large scale, it leads to an abundance of problems. Valves are impaired by the globules of resin, pipes can block, and apparatus may be subject to greater wear due to mechanical friction. The globules of resin are porous and therefore have a large inner surface area (about 825 m$^2$/gram resin). Sterilisation becomes a problem, as air enclosed in the resin is not autoclaved. Thus, the process cannot be practicably carried out on a large scale using resin addition during cultivation of the microorganisms that produce epothilones.

Therefore an advanced process for the production of epothilones, especially of epothilones A and B, was found and described in WO 99/42602. That method comprises complexing of epothilones from culture media of epothilone-producing microorganisms, said media comprising cyclodextrines or other complex-forming agents, mixing of the cell-free culture medium (e.g. filtrate or centrifugate of said culture medium) with a synthetic resin, for example a resin based on styrene/divinylbenzene copolymers as matrix, such as Amberlite XAD-16 (Rohm & Haas Germany GmbH, Frankfurt, Germany) or Diaion HP-20 (Resindion S.R.L., Mitsubishi Chemical Co., Milan, Italy) in order to absorb the epothilones and desorption, especially with an alcohol, most preferably isopropanol. This is followed by addition of water to the alcohol phase, removal of the solvent phase (preferably by evaporation), phase separation of the resulting residue in the presence of an ester, especially ethyl acetate or isopropyl acetate, usually molecular filtration (gel chromatography) of the dried ester phase, separation of the resulting epothilone mixture by reverse phase HPLC (preferably by elution with a mixture of nitrile/water, e.g. acetonitrile/water), and optionally further purification by phase separation in the presence of a water/ether mixture, preferably subsequent adsorption chromatography on silica gel in order to achieve further removal of impurities, and crystallisation/recrystallisation.

Though a useful progress and appropriate for industrial scale production, this method still suffers from certain disadvantages.

For example, in order to obtain sufficient purity, it is advisable to make use of either the molecular filtration step or the silica gel adsorption chromatography step or both. More difficulties come from the phase separation in the presence of an ester, such as ethyl acetate, which (especially due to the long time for phase separation of the water/ester phase in large industrial scale) is very time-consuming, as well as the subsequent evaporation, which in addition is difficult to handle in view of foaming and sputtering.

It is thus a problem to be solved by the present invention to avoid as many of the above difficulties as possible and find new and advantageous ways for the isolation of epothilones, especially epothilones A and B, after their adsorption to a resin.

GENERAL DESCRIPTION OF THE INVENTION

Very surprisingly, it has now been found that by simple replacement of the alcohols used as desorption solvent with certain other solvents (named weakly polar or apolar solvents as specified below) provides a real breakthrough that can be achieved in order to obtain a solution to the problems mentioned above, leading to additional advantages such as improved desorption and higher final yield. Among the additional advantages are (i) higher selectivity of desorption; (ii) higher amount of desorbed epothilones, indicating more complete desorption; (iii) no re-extraction with ester (e.g. ethyl acetate) with the highly problematic water/ester phase separation and no subsequent ether evaporation required; (iv) no molecular filtration and usually no adsorption chromatography are required; (v) the time required for desorption is diminished considerably; (vi) fewer process steps, (vii) diminished contamination risk (important with the highly toxic epothilones), and/or (viii) better and safer handling (depending on the solvent used for desorption=extraction); and (ix) also depending on the solvent unexpectedly even lower amounts of by-products or impurities with similar polarity as the epothilones, especially as epothilone B, need to be removed after reversed phase chromatography. These and further advantages can be deduced from the details given in the subsequent Detailed Description of the Invention:

DETAILED DESCRIPTION OF THE INVENTION

One aspect of the invention relates to a process for desorbing epothilones, especially epothilone A and/or B, in particular epothilone B, from a resin, especially a synthetic resin, with a weakly polar or apolar solvent.

A further aspect relates to a process for working up (or purifying) epothilones, especially after their production in a standard medium for chemical synthesis or preferably a culture medium which comprises microorganisms, especially myxobacteria, in particular of the genus *Sorangium*, which are suitable for producing epothilones, especially epothilone A and/or B, and a complex-forming component, said process comprising the use of a weakly polar or apolar solvent for the desorption of said epothilones from a resin.

A third aspect of the invention relates to the use of a weakly polar or apolar solvent for the desorption of epothilones, especially epothilone A and/or B, in particular epothilone B, from a resin, especially a synthetic resin.

The general terms used hereinabove and hereinbelow preferably have the meanings given hereinbelow:

The term "epothilones" preferably relates to any epothilone or epothilone derivative mentioned in the patent applications WO 99/03848, WO 00/49020, WO 00/49021, WO 00/47584, WO 00/00485, WO 00/23452, WO 99/03848, WO 00/49019, WO 99/07692, WO 98/22461, WO 99/65913, WO 98/38192, WO 00/50423, WO 00/22139, WO 99/58534, WO 97/19086, WO 98/25929, WO 99/67252, WO 99/67253, WO 00/31247, WO 99/42602, WO 99/28324, WO 00/50423, WO 00/39276, WO 99/27890, WO 99/54319, WO 99/54318, WO 99/02514, WO 99/59985, WO 00/37473, WO 98/08849, U.S. Pat. No. 6,043,372, U.S. Pat. No. 5,969,145, WO 99/40047, WO 99/01124, and/or WO 99/43653, more preferably to epothilone A and especially epothilone B, but in a broader aspect of the invention also to the epothilones D and E, described in WO 97/19086 and WO 98/22461, the epothilones E and F, described in WO 98/22461, or the epothilones described in WO 99/02514. All these documents, especially with regard to the epothilone derivatives and the preferred epothilone derivatives mentioned therein, are herewith enclosed by reference.

A weakly polar or apolar solvent preferably has the following characteristics:

Preferred is a solvent that, in the eluotropic row determined according to Snyder et al., J. Chromatogr. Sci. 16, 223 (1978), shows the following characteristics, where $x_e$ is the proton acceptor parameter (indicator of the tendency to form hydrogen bonds as hydrogen acceptor), $X_d$ is the proton donor parameter (indicator of the tendency to form hydrogen bonds as hydrogen donor) and $x_n$ is the dipole parameter (indicating the dipole character), with the proviso that $x_e+x_d+x_n=1$, or a mixture of such solvents:

$x_e$=0.20-0.40; $x_d$=0.15-0.36; and $x_n$=0.38-0.60; preferably $x_e$=0.22-0.32; $x_d$=0.17-0.34; and $x_n$=0.39-0.54.

Very preferred among the weakly polar or apolar solvents are lower alkyl-lower alkyl ketones or cyclic ketones, such as acetone, methyl ethyl ketone, 2-pentanone, methyl-isobutyl-ketone or cyclohexanone, more preferably ethers, especially cyclic ethers, more especially tetrahydrofuran or dioxan; still more preferably aliphatic halogen compounds, especially lower alkyl halogenides, especially methylene dichloride (=methylenechloride) or ethylene dichloride; or most especially aromatic solvents, especially naphthalene or (preferably) benzene or naphthaline or (preferably) benzene substituted by one or more, preferably one to three moieties selected from the group consisting of lower alkyl, especially methyl, ethyl or isopropyl, lower alkoxy, especially methoxy or ethoxy, halogen, especially fluoro, chloro, bromo or iodo, nitro and lower alkoxy-lower alkyl, especially ethoxymethyl; especially toluene, ethyl-benzene, xylene, especially o-, m- or p-xylene, mesitylene, pseudo-cumene, hemellitene, cumene, isopropyl-toluene, phenyl halogenides, especially fluorobenzene, chlorobenzene, bromobenzene or iodobenzene, lower alkoxy benzenes, especially ethoxybenzene or methoxybenzene, or lower alkoxy-lower alkyl benzenes, especially ethoxymethyl benzene (benzyl ether); or any mixture of two or more, for example 2 to 4 of these solvents; most preferred are lower alkyl-benzenes, especially ethyl-benzene, xylene, especially o-, m- or p-xylene, mesitylene, pseudo-cumene, hemellitene, cumene, isopropyl-toluene, and most especially toluene.

The term "weakly polar or apolar solvent" also includes mixtures of two or more of the solvents described hereinbefore and hereinafter, e.g. of 2 to 4 such solvents.

The prefix "lower" always indicates that the correspondingly named radical contains preferably up to a maximum of 7 carbon atoms, in particular up to 4 carbon atoms, and is branched or unbranched. Lower alkyl may be for example unbranched or branched once or more, and is e.g. methyl, ethyl, propyl such as isopropyl or n-propyl, butyl such as isobutyl, sec-butyl, tert-butyl or n-butyl, or also pentyl such as amyl or n-pentyl.

Halogen is preferably iodo, bromo, chloro or fluoro.

A hydrocarbon preferably is an organic compound having 4 to 32, more preferably 4 to 20, still more preferably 6 to 16 carbon atoms and may be aliphatic, e.g. a linear, branched or cyclic saturated alkane, e.g. cyclohexane, a linear, branched or cyclic (non-aromatic) organic compound with one or more double and/or triple bonds, or an aromatic hydrocarbon, the latter being unsubstituted or substituted by one or more, e.g.

up to three, substituents selected from the group consisting of lower alkyl, especially methyl, ethyl or isopropyl, lower alkoxy, especially methoxy or ethoxy, halogen, especially fluoro, chloro, bromo or iodo, nitro and lower alkoxy-lower alkyl, especially ethoxymethyl; preferably by one to three lower alkyl moieties.

An alcohol is preferably a hydroxy-lower alkane, especially methanol, ethanol or n- or isopropanol.

A resin is especially a synthetic resin, preferably a resin based on styrene and divinylbenzene copolymers, more preferably Amberlite XAD-4 or preferably Amberlite XAD-16 [Rohm & Haas Germany GmbH, Frankfurt] or Diaion HP-20 [Resindion S.R.L., Mitsubishi Chemical Co., Milan]. It goes without saying that a resin from which an epothilone or epothilones are to be desorbed in accordance with the invention has epothilones non-covalently in contact with it (e.g. reversibly bound to it or adsorbed to it). In other terms, where the term "resin" is used, it is intended to mean "resin having one or more epothilones in contact with it, especially reversibly bound or adsorbed to it".

PREFERRED ASPECTS OF THE INVENTION

In a preferred aspect of the invention, the invention relates to a process comprising a desorption from a resin with a weakly polar or apolar solvent as described above or below, comprising any further purification steps desirable or required to come to the respective epothilones, especially epothilone A and most especially epothilone B, in pure form, preferably those described as preferable in the present invention.

Working up of the epothilones is preceded by the reaction or process leading to a reaction product comprising epothilones to be worked up which are isolated (i) either from chemical reaction mixtures after solution in an appropriate polar aqueous medium, or (ii) more preferably from the supernatant (for example a cyclodextrine containing one as described in WO 99/42602) of a culture medium with microorganisms producing the epothilones by separating a culture into the liquid phase (e.g. centrifugate or filtrate) and solid phase (cells), especially by means of filtration or centrifugation (tubular centrifuge or separator).

This pretreatment is then preferably continued by directly mixing the solution ((i)) or liquid phase ((ii)) with a resin, especially a synthetic resin, especially a resin based on styrene and divinylbenzene copolymers as matrix (hereinafter referred to also simply as polystyrene resin), such as Amberlite XAD-16 or Diaion HP-20 (preferably in a ratio of centrifugate: resin volume of ca. 10:1 to 100:1, preferably about 50:1). After a period of contact of preferably 0.25 to 50 hours, especially 0.8 to 22 hours, the resin is separated, for example by filtration, sedimentation or centrifugation. If required, after adsorption the resin is washed with a strongly polar solvent, preferably with water.

Then the preferred process of working up according to the present invention starts: Desorption of the epothilones (as such forming a very preferred aspect of the invention) is effected with a weakly polar or apolar solvent, in particular with lower alkyl halogenides, especially methylene dichloride or ethylene dichloride, or more preferably aromatic solvents, especially naphthalene or (preferably) benzene, or naphthaline or (preferably) benzene substituted by one or more, preferably one to three moieties selected from the group consisting of lower alkyl, especially methyl, ethyl or isopropyl, lower alkoxy, especially methoxy or ethoxy, halogen, especially fluoro, chloro, bromo or iodo, nitro and lower alkoxy-lower alkyl, especially ethoxymethyl; most preferably toluene. The step of extraction may be repeated one or more times, preferably 0 to 3 times, especially once, in order to obtain more complete desorption where necessary or desired.

The working up of the (in case of repeated extraction combined) solutions of desorbed epothilones thus obtainable preferably continues with the removal of the solvent used for desorption from the resulting solutions by evaporation (distillation), preferably by means of concentration in a reactor and subsequently in a rotary evaporator under vacuum.

Subsequently, further processing takes place using the following steps, where the purification step by means of reversed-phase chromatography with elution with a nitrile is compulsory, while the other steps are optional:

crystallization of the epothilone(s) after desorption; especially, for the crystallization of epothilone B, a mixture of an alcohol and a hydrocarbon, especially of a lower alkanol and a cyclic aliphatic hydrocarbon with 3 to 10 ring atoms, most especially of methanol and cyclohexane (preferably in a v/v ratio of 1:10 to 10:1, especially of 1:3 to 3:1, is added. Addition of water leads to fast phase separation, and the alcohol phase is evaporated to dryness, e.g. by means of a rotary evaporator under vacuum. The resulting extract which comprises the epothilone B is afterwards crystallized from an appropriate solvent mixture, especially from an alcohol/cyclic aliphatic hydrocarbon mixture, most preferably isopropanol/cyclohexane, preferably in a v/v ratio of 1:10 to 10:1, more preferably 1:6 to 6:1, most preferably 1:6 to 1:4;

(obligatory) separation of the epothilones by reversed-phase chromatography after being taken up in a suitable solvent, especially a mixture of a nitrile and water, preferably acetonitrile/water, in a preferred v/v ratio of 1:10 to 10:1, especially 1:3 to 1:1, and elution with a mixture of nitrile and water, preferably characterised in that the chromatography is carried out on column of a reversed phase material, which is charged with hydrocarbon chains, such as hydrocarbon chains containing 18 carbon atoms, especially an RP-18 material, and an eluant comprising a nitrile, especially a lower alkylnitrile, in particular acetonitrile, is used, in particular a mixture of nitrile/water is used, especially a mixture of acetonitrile/water, preferably in a ratio of nitrile to water of about 1:99 to 99:1, primarily between 1:9 and 9:1, e.g. between 2:8 and 7:3, e.g. 3:7 or 4:6; and removal of the nitrile from the collected epothilone (especially epothilone A or most especially epothilone B) comprising fractions by evaporation (distillation); if desired, the remaining water with the epothilone is then extracted with an ester, especially a lower alkyl-lower alkanoate, preferably isopropyl acetate, with subsequent evaporation (preferably first in a reactor, then in a rotary evaporator under vacuum) of the epothilone containing ester phase to dryness; (if required, the starting epothilone solution may be split and separated in more than one reverse phase separate runs;)

only if required (e.g. as an alternative to the crystallization after desorption) adsorption chromatography, in particular by adding to a column of silica gel and eluting with an appropriate solvent or solvent mixture, especially a mixture of ester/hydrocarbon, for example lower alkyl alkanoate/$C_4$-$C_{10}$-alkane, especially ethyl or isopropyl acetate/n-hexane, in which the ratio between the ester and hydrocarbon is preferably in the range 99:1 to 1:99, preferably 10:1 to 1:10, for example 4:1;

and finally recrystallisation, e.g. from appropriate solvents or solvent mixtures, for example consisting of esters, ester/hydrocarbon mixtures or alcohols, especially ethyl or isopropyl acetate:toluene 1:10 to 10:1, preferably 2:3 (epothilone A) or methanol or ethyl acetate (epothilone B);

in which process, if necessary and/or desired, between each step being employed, the resulting solutions or suspensions are concentrated, and/or liquid and solid components are separated from one another, in particular by sedimenting, filtering or centrifuging of solutions/suspensions. The more precise definitions mentioned above and below can be preferably used in the above individual steps.

A preferred aspect of the invention relates also to a process for the isolation of epothilones adsorbed to a synthetic resin, especially epothilone A or most especially epothilone B, which process comprises (i) the desorption of the epothilones from said synthetic resin with a weakly polar or apolar solvent, in particular with lower alkyl halogenides, especially methylene dichloride or ethylene dichloride, or more preferably aromatic solvents, especially naphthalene or (preferably) benzene, or naphthaline or (preferably) benzene substituted by one or more, preferably one to three moieties selected from the group consisting of lower alkyl, especially methyl, ethyl or isopropyl, lower alkoxy, especially methoxy or ethoxy, halogen, especially fluoro, chloro, bromo or iodo, nitro and lower alkoxy-lower alkyl, especially ethoxymethyl; most preferably toluene; or in a broader aspect of the invention a mixture of two or more such solvents; and (ii) separation of the epothilones by reversed-phase chromatography after being taken up in a suitable solvent, especially a mixture of a nitrile and water, preferably acetonitrile/water, in a preferred v/v ratio of 1:10 to 10:1, especially 1:3 to 1:1, and elution with a mixture of nitrile and water, preferably characterised in that the chromatography is carried out on column of a reversed phase material, especially an RP-18 material, which is charged with hydrocarbon chains, such as hydrocarbon chains containing 18 carbon atoms, and an eluant comprising a nitrile, especially a lower alkylnitrile, in particular acetonitrile, is used, in particular a mixture of nitrile/water is used, especially a mixture of acetonitrile/water, preferably in a ratio of nitrile to water of about 1:99 to 99:1, primarily between 1:9 and 9:1, e.g. between 2:8 and 7:3, e.g. 3:7 or 4:6.

In a further preferred aspect of the invention, the process in the last paragraph starting with step (i) and comprising step (ii) further implies any further purification steps desirable or required to come to the respective epothilones, especially epothilone A and most especially epothilone B, in pure form, preferably those described as preferable in the present invention.

Preparation for working up is preferably carried out as follows: Adsorption of the epothilones, especially from chemical reaction mixtures or more preferably from the supernatant of cultures of microorganisms, can be achieved as described in WO 99/42602 or in analogy thereto; briefly, the epothilones are found in the centrifugate, which is then directly mixed with a synthetic resin, especially a styrene/divinylbenzene copolymer resin, such as Amberlite XAD-16 or Diaion HP-20 (preferably in a ratio of centrifugate:resin volume of ca. 10:1 to 100:1, preferably about 50:1) and stirred in an agitator. In this step, the epothilones are transferred to the resin. After a period sufficient for adsorption, e.g. period of contact of ca. 0.2 to 10 h, the resin is separated by centrifugation or filtration. Adsorption of the epothilones onto the resin may also be effected in a chromatography column, by placing the resin in the column and running the centrifugate over the resin. After adsorption, the resin is washed with water.

The preferred processes according to the invention then start and proceed as follows: Desorption of the epothilones from the resin is preferably effected with a weakly polar or apolar solvent according to the invention, especially one described as preferred above or below, especially methylenechloride or most especially toluene. The solvent is then removed as far as necessary, preferably until a dry residue is obtained. Where appropriate, the residue is taken up in an alcohol/hydrocarbon mixture, especially in methanol/cyclohexane, preferably in the ratios described above, in a relatively low volume. The alcohol phase is evaporated, preferably to dryness, and the alcohol extract is then crystallized from a mixture of an alcohol, especially iso-propanol, and a hydrocarbon, especially cyclohexane, preferably in the ratios described above. The resulting solid crystallized material is then dissolved in a nitrile/water mixture, preferably as described above, especially a 2:3 (v/v) acetonitrile/water mixture, and the resulting feed solution is poured, if required, after splitting in more than one run, onto a preparative reversed phase column. Elution with nitrile/water, especially as just mentioned, follows. The (aceto-)nitrile of the resulting fractions containing epothilone, especially epothilone A and most especially epothilone B, is removed by evaporation (distillation), and the resulting water phase is extracted with an ester, especially isopropyl acetate. The ester extract is then evaporated, preferably to dryness, and subsequently the resulting material is recrystallized, for example an epothilone A fraction is crystallised directly from an ester/hydrocarbon mixture, e.g. ethyl acetate:toluene=2:3, and the epothilone B fraction from an ester, especially ethyl acetate or preferably from an alcohol, especially methanol.

Especially with toluene a highly selective eluent (desorbant) has been discovered which allows to achieve an approximately 100% yield in half of the desorption time needed with isopropanol used in WO 99/42602. Surprisingly, the amount of desorbed epothilones is increased, e.g. to 130% after desorption with toluene when compared with isopropanol desorption. (Though this appears prima facie impossible from a theoretical point of view, it nicely illustrates a major advantage of the present invention: The result is related to the assay of the loaded resin. As that assay made use of isopropanol for desorption, an incomplete desorption procedure had to be taken as basis leading originally to lower assay values which now turn out to be deceptive). The epothilone mixture can (without or with preceding crystallization) be applied directly to the reverse phase column. The process becomes highly robust with regard to the solvent amounts, the stirring rates and temperatures. While for alcohols (e.g. ethanol or isopropanol) under stirring a two-phase desorption can be shown where a first amount of epothilone comprising material is desorbed in a first period of time (explainable possibly by the pore size distribution found in polystyrene XAD-16 which has two maxima of distribution), a second amount after a further period of time, this undesirable behaviour is not found with toluene or also dichloromethane where all material is desorbed already in the first period of time. Under comparable conditions, the evaporation residue in the case of isopropanol for epothilones A and B in one example has been found to be 40 g, with methylene chloride 3.3 g, in the case of toluene only 0.9 g, with e.g. 17-18 g-% of epothilone B after desorption from styrene/divinylbenzene copolymer resins obtained from cyclodextrine-comprising culture supernatants as described in WO 99/42602, indicating much higher purity. While toluene has the most significant advantages, dichloromethane has as one advantage the ease of removal, due to the low boiling point.

The separation of epothilon A and B can also be achieved by performing the chromatography disclosed herein in its simulated moving bed (SMB) approach. SMB-chromatographies are widely used for the separation of binary mixtures, e.g., the separation of racemates on chiral stationary phases, e.g., the SORBEX processes in the petrochemical industries, like Parex or Molex, or the SAREX process in the sugar industry. Compared to batch chromatography SMB-chromatography provides the advantage of a continous countercurrent unit operation, which leads to increased productivity and reduced mobile phase consumption. Several systematic procedures for the method development of SMB-chromatographies are known to the person skilled in the art. Such procedures are described, e.g., by R. -M. Nicoud, M. Bailly, J. Kinkel, R. M. Devant, T. R. E. Hampe and E. Küsters in *Proceedings of the 1st European Meeting on Simulated Moving Bed Chromatography*, (1993), ISBN 2-905-267-21-6, p. 65-88; E. Küsters, G. Gerber and F. D. Antia, *Chromatographia*, 40 (1995) 387; T. Pröll and E. Küsters, *J. Chromatogr. A*, 800 (1998) 135; or C. Heuer, E. Küsters, T. Plattner and A. Seidel-Morgenstern, *J. Chromatogr. A*, 827 (1998) 175.

The basic parameters for the separation of epothilon A and B with SMB chromatography can be taken directly from the conventional LC separation. Preferably, reversed phase silica gel (RP 18) is taken as stationary phase and water/acetonitrile-mixtures as mobile phases. The final set of flow rates (for the individual SMB zones and the switching time, respectively) can be taken either from a simple flow scheme as developed by E. Küsters, et al in *Chromatographia*, 40 (1995) 387 or after careful estimation of adsorption isotherms as laid down in *J. Chromatogr. A*, 800 (1998) 135 and *J. Chromatogr. A*, 827 (1998) 175. The work up of extract and raffinate streams can again be performed as described for the conventional LC separation.

The invention most preferably relates to the processes and methods described in the subsequent examples.

EXAMPLES

The following Examples serve to illustrate the invention without limiting its scope.

Caution: When handling epothilones, appropriate protective measures must be taken, where necessary, in view of their high toxicity.

Example 1

Work-up Procedure for Epothilone B

Desorption of 591.7 kg of charged resin (styrene/divinylbenzene copolymer resin XAD-16 charged with epothilones A and B from a culture medium) is effected by stirring the resin in two portions each with 720 liters of toluene in four portions for appr. 8 hours. Separation of the toluene phase from the resin takes place using a suction filter. The combined toluene phases are washed in two portions with each 250 l of water. After phase separation, the toluene extract is concentrated in a 1000 liters reactor to approximately 20-40 liters and afterwards concentrated to dryness in a rotary evaporator under vacuum. The result is a toluene extract of 4.095 kg containing 209 g of epothilone B. The toluene extract is dissolved in 16.5 liters of methanol and 24.5 liters of cyclohexane. After addition of 0.8 liters of water phase separation occurs immediately. The methanol fraction is evaporated to dryness in a rotary evaporator under vacuum yielding 1.025 kg evaporation residue containing 194 g of epothilone B. The methanol extract is afterwards being crystallized in a solvent mixture consisting of 2.05 liters isopropanol and 10.25 liters cyclohexane, yielding 0.4 kg crystallized material containing 184 g of epothilone B. The crystals are dissolved in 3.2 liters acetonitrile/water=⅔ (v/v) and the resulting feed solution is transferred in three separate runs onto a preparative reversed phase column (25 kg RP-18 spherical silica gel, YMC-Gel ODS-A 120; 5-15 μm; Waters Corp., Milford, Mass., USA). Elution is effected with acetonitrile/water=⅔ (v/v) as mobile phase with a flow rate of 2.3 liters/min; retention time of epothilone A=77-96 min, retention time of epothilone B 96-119 min. Fractionation is monitored with a UV detector at 250 nm. The acetonitrile of the combined epothilone B fractions (of the three runs) is distilled off and the remaining water phase is extracted with 504 liters of isopropyl acetate. The isopropyl acetate extract is concentrated in a 630 liters reactor to approximately 20-40 liters and afterwards concentrated to dryness in a rotary evaporator under vacuum. The weight of the evaporation residue of the epothilone B fractions is 170 g and it has a content of 98.4% according to HPLC (external standard). The resulting material is finally crystallized in 2.89 liters of methanol at 0-5° C. yielding 150 g of epothilone B pure crystallisate.

Melting point: 124-125° C.; $^1$H-NMR data for epothilone B (500 MHz-NMR, solvent: DMSO-d6. Chemical displacement δ in ppm relatively to TMS. S=singlet, d=doublet, m=multiplet):

| δ (Multiplicity) | Integral (number of H) |
|---|---|
| 7.34 (s) | 1 |
| 6.50 (s) | 1 |
| 5.28 (d) | 1 |
| 5.08 (d) | 1 |
| 4.46 (d) | 1 |
| 4.08 (m) | 1 |
| 3.47 (m) | 1 |
| 3.11 (m) | 1 |
| 2.83 (dd) | 1 |
| 2.64 (s) | 3 |
| 2.36 (m) | 2 |
| 2.09 (s) | 3 |
| 2.04 (m) | 1 |
| 1.83 (m) | 1 |
| 1.61 (m) | 1 |
| 1.47-1.24 (m) | 4 |
| 1.18 (s) | 6 |
| 1.13 (m) | 2 |
| 1.06 (d) | 3 |
| 0.89 (d + s, overlapping) | 6 |
| Σ = | 41 |

Example 2

Comparison of Different Desorption Processes for Epothilone B Preparation 360 ml each of an aqueous suspension of the styrene/divinylbenzene copolymer resin XAD-16 charged with epothilone A and B from a culture of myxobacteria by the method described in WO 99/42602 (corresponding to 194 g wet Amberlite® XAD-16) are extracted with the solvents and under the conditions mentioned in the subsequent table in a stirred (common lab anchor stirrer) glas reactor with a sintered frit at the bottom (home made solid phase batch reactor, inner diameter 10 cm×20 cm lengths, "Stirrer/Frit" hereinafter).

(boiling point of methylene chloride is about 40° C., that of isopropanol 81-83° C.), the time-intensive and very problematic ethyl acetate/water phase separation is no longer

TABLE 1

Comparison of Desorption methods for the manufacture of Epothilone B
Starting resin (resin with adsorbed epothilone):
1001 theoretical load 70 mg per 360 ml resin suspension (corresponds to
70 mg per 194 g of wet XAD-16)
1003 theoretical load 114 mg per 360 ml resin suspension (corresponds to
114 mg per 194 g of wet XAD-16)

| Variant | 1 | 2 | 3 | 4 | 5 | 6 |
|---|---|---|---|---|---|---|
| Reactor | Stirrer/Frit (RT) | Stirrer/Frit (RT) | Stirrer/Frit (RT) | Stirrer/Frit (RT) | Reflux (40° C.) | Refl. (42-45° C.) |
| Starting Resin | #1001 | #1001 | #1003 | #1003 | #1003 | #1003 |
| Amount of Resin Suspension (ml) | 360 | 360 | 360 | 360 | 360 | 180 |
| Desorption Solvent | Isopropanol | Methylenchloride | Isopropanol | Methylenchloride | Methylenchloride | Isopropanol |
| Stirring (rpm) | 250 | 250 | 250 | 250 | 250 | 250 |
| Volume (l) | 8 × 0.2 = 1.6 | 3 × 0.36 = 1.1[a] | 5 × 0.72[i] = 3.6 | 3 × 0.72[h] = 2.2 | 1 × 2.2 | 1 × 1.8 |
| Desorption time (h) | 8 | 3 | 5 | 3 | 2 | 2 |
| Evaporation (h) | 2[e] | 0.5 | 4[e] | None | None | 2 |
| Water addition (l) | 0.7 | None[b] | 1.15 | None | None | 0.54 |
| Extraction with ethyl acetate (l) | 1.1 | None | 2.2 | None | None | 1.1 |
| Phase separation time (h) | 24[c] | None | 15 | None | None | 15 |
| Evaporation (h) | 2 | None | 2 | 1 | 1 | 1 |
| Evaporation Residue (g) | 5.84[f] | 3.37[d] | 3.31 | 2.68[d] | 3.24[f] | 1.70 |
| Content (%) | 1.26 | 1.75 | 2.9 | 3.7 | 3.1 | 3.3 |
| Yield: mg (%) | 74 (105)[g] | 59 (84) | 96 (84) | 99 (87) | 101 (89) | 56 (98) |
| Variant | 7 | 8 | 9 | 10 | 11 | 12 |
| Reactor | Erl./mag. St.* | Stirrer/Frit (RT) | Reflux (42-45° C.) | Stirrer/Frit (RT) | Stir./Frit (RT) | Stir./Frit (43° C.) |
| Starting Resin | #1003 | #1003 | #1003 | #1003 | #1003 | #1003 |
| Amount of Resin Suspension (ml) | 100 | 360 | 180 | 360 | 360 | 360 |
| Desorption Solvent | Methylenchl. | Toluene | Isopropanol | Toluene | Toluene | Toluene |
| Stirring (rpm) | ? | 640 | 250 | 250 | 640 | 250 |
| Volume (l) | 1 × 0.5 = 0.5 | 3 × 0.72 = 2.2 | 1 × 1.8 = 1.8 | 4 × 0.36 = 1.44 | 4 × 0.36 = 1.44 | 4 × 0.36 = 1.44 |
| Desorption time (h) | 5 | 3 | 6 | 4 | 4 | 4 |
| Evaporation (h) | None | | 6 | None | None | None |
| Water addition (l) | None | 0.5[j] | 0.54 | 0.5[k] | 0.5[k] | 0.5[k] |
| Extraction with ethyl acetate (l) | None | None | 1.1 | None | None | None |
| Phase separation time (h) | None | 0.1 | 15 | 0.1 | 0.1 | 0.1 |
| Evaporation (h) | 1 | 1 | 1 | 1 | 1 | 1 |
| Evaporation Residue (g) | 4.38 | 0.88 | 2.32 | 0.75 | 0.88 | 0.95 |
| Content (%) | 0.5 | 17.4 | 2.69 | 17.6 | 17.1 | 15.8 |
| Yield: mg (%) | 22 (69) | 153 (134) | 62.5 (110) | 132 (116)[l] | 150 (132) | 150 (132) |

[a]Not optimized; in case of 2 extractions about 5% yield are lost.
[b]3-fold back-extraction with water removes no polar component
[c]First of 3 phase separations overnight
[d]The material, when compared to ethyl acetate-evaporation residue, can be chromatographed much better on silica gel
[e]Corresponds to an evaporation residue of about 25 to 30 g
[f]Drying oven (high vacuum) over the weekend
[g]Possibly a result of the, concerning the time used, generous first phase separation
[h]Recovery: 1st extraction = 700 ml; 2nd extraction = 660 ml; 3rd extraction = 680 ml
[i]Recovery: 1st extraction = 670 ml; 2nd extraction = 710 ml; 3rd extraction = 720 ml
[j]The necessity of water addition has not yet been confirmed
[k]Simplifies the removal of the water originally present (XAD-16 is covered by water as used)
[l]In view of the results of variant 8, 11 and 12 and the elution curves for all experiments with toluene, the use of a smaller amount of resin cannot be excluded.
"Erl./mag. St." stands for magnetic stirring in an Erlenmeyer flask.
"Methylenchloride" ("Methylenchl.") is dichloromethane
"Stir./Frit" stands for Stirrer/Frit
"RT" stands for room temperature From these experiments and further data, it can be deduced that in comparison with isopropanol the methylenechloride extraction offers better selectivity, a shorter time of extraction (approximately by a factor of 2), faster solvent distillation required, the second solvent distillation is no more required, so that a lower number of process steps, resulting in lower contamination risk, better and safer handling, can be used; workup in half of the volume (e.g. in 1000 l reactors instead of 2000 l reactors) is possible; the product epothilone B has a better purity profile (fewer by-products with comparable polarity as epothilone B), and the evaporation residue does not sputter and foam as in the case with the ethal acetate extraction. For desorption with toluene, a higher yield is obtained in comparison to isopropanol extraction (about 100 instead of about 80%), better selectivity can be observed (with isopropanol, about the tenfold amount of by-products is desorbed), the extraction time is shortened considerably (by a factor of about 3), the difficult filtration after desorption with isopropanol is simplified (the isopropanol extraction was difficult to implement in larger scale), the second solvent distillation is no longer required, work-up is possible in smaller reactors (again, for example, it is possible to use a 1000 l instead of a 2000 l reactor), it is possible to abandon the silica gel chromatography (the evaporation residue after desorption contains already about 40% of an epothilone A/B-mixture), and the evaporation residue after desorption does not show the foaming and sputtering observed for the residue from ethyl acetate extraction.

What is claimed is:

1. A process for the isolation of epothilones adsorbed to a synthetic resin which process comprises
   (iii) the desorption of the epothilones from said synthetic resin with a weakly polar or apolar solvent; and
   (iv) separation of the epothilones by reversed-phase chromatography after being taken up in a suitable solvent and elution with a mixture of nitrile and water.

2. A process for isolating epothilones from a reaction mixture, said process comprising desorbing the epothilones from a synthetic resin with a weakly polar or apolar solvent, where the step of desorption may be repeated in order to achieve more complete desorption;
   removing the solvent used for desorption from the resulting solutions by evaporation;
   optionally crystallizing the epothilone(s) after desorption; especially, for the crystallization of epothilone B, adding a mixture of an alcohol and a hydrocarbon and evaporating the alcohol phase to dryness, and crystallizing the epothilone B from an appropriate solvent mixture;
   (obligatory step) separating the epothilones by reversed-phase chromatography by taking up the residue from the preceding step in a suitable solvent and eluting with a mixture of nitrile and water and removing the nitrile from the collected epothilone comprising fractions by evaporation; if desired, the remaining water with the epothilone is then extracted with an ester with subsequent evaporation of the epothilone containing ester phase to dryness;
   optionally further purifying by adsorption chromatography;
   and finally recrystallizing a purified epothilone from appropriate solvents or solvent mixtures; in which process, if necessary and/or desired, between each step being employed, the resulting solutions or suspensions are concentrated, and/or liquid and solid components are separated from one another.

3. A process according to claim 2, where desorption of the epothilones from the resin is effected with a weakly polar or apolar solvent; the solvent is then removed as far as necessary, preferably until a dry residue is obtained, where appropriate, the residue is taken up in an alcohol/hydrocarbon mixture in a relatively low volume; the alcohol phase is evaporated, preferably to dryness, and the alcohol extract is then crystallized from a mixture of an alcohol and a hydrocarbon the resulting solid crystallized material is then dissolved in a nitrile/water mixture, especially a 2:3 (v/v) acetonitrile/water mixture, and the resulting feed solution is poured, if required, after splitting in more than one run, onto the preparative reversed phase column; followed by elution with nitrile/water; then removal of the nitrile of the resulting fractions containing epothilone by evaporation follows and the resulting water phase is extracted with an ester; said ester extract is then evaporated and, subsequently the resulting material is recrystallized.

4. A process according to claim 1 wherein the separation of epothilone A and B is achieved by simulated moving bed (SMB) chromatography.

5. A process according to claim 2, wherein the weakly polar or apolar solvent is selected from the group consisting of lower alkyl halogenides and aromatic solvents, especially naphthalene, benzene or naphthalene or benzene substituted by one or more moieties selected from the group consisting of lower alkyl, lower alkoxy, halogen, nitro and lower alkoxy-lower alkyl; or a mixture of two or more such solvents; the resin is a synthetic resin.

* * * * *

UNITED STATES PATENT AND TRADEMARK OFFICE
CERTIFICATE OF CORRECTION

PATENT NO. : 7,569,698 B2  
APPLICATION NO. : 11/205892  
DATED : August 4, 2009  
INVENTOR(S) : Kuesters et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 661 days.

Signed and Sealed this  
Third Day of May, 2011

David J. Kappos  
*Director of the United States Patent and Trademark Office*